US008747875B2

(12) United States Patent
Hemsarth et al.

(10) Patent No.: US 8,747,875 B2
(45) Date of Patent: Jun. 10, 2014

(54) PHOTO-STABLE PEST CONTROL

(75) Inventors: W. Lance H. Hemsarth, Ringwood, NJ (US); Linda Valencia, Belleville, NJ (US)

(73) Assignee: The Hartz Mountain Corporation, Seacaucus, NJ (US)

(*) Notice: Subject to any disclaimer, the term of this patent is extended or adjusted under 35 U.S.C. 154(b) by 387 days.

(21) Appl. No.: 13/121,054

(22) PCT Filed: Sep. 25, 2009

(86) PCT No.: PCT/US2009/058363
§ 371 (c)(1),
(2), (4) Date: May 19, 2011

(87) PCT Pub. No.: WO2010/036882
PCT Pub. Date: Apr. 1, 2010

(65) Prior Publication Data
US 2011/0224296 A1 Sep. 15, 2011

Related U.S. Application Data

(60) Provisional application No. 61/100,903, filed on Sep. 29, 2008.

(51) Int. Cl.
*A01N 25/02* (2006.01)
*A01N 53/00* (2006.01)
*A01N 25/00* (2006.01)
*A01N 37/10* (2006.01)
*A01N 37/18* (2006.01)

(52) U.S. Cl.
CPC .............. *A01N 25/006* (2013.01); *A01N 25/02* (2013.01); *A01N 37/10* (2013.01); *A01N 37/18* (2013.01); *A01N 53/00* (2013.01)
USPC ............ 424/406; 424/405; 514/65; 514/531; 514/543; 514/613

(58) Field of Classification Search
CPC ..... A01N 25/006; A01N 25/02; A01N 37/10; A01N 37/18; A01N 53/00
USPC .................... 514/531, 543, 613, 65
See application file for complete search history.

(56) References Cited

U.S. PATENT DOCUMENTS

| | | |
|---|---|---|
| 3,560,613 A | 2/1971 | Miskus et al. |
| 3,682,943 A | 8/1972 | Hoffman et al. |
| 3,886,274 A | 5/1975 | Kristinsson et al. |
| 3,943,239 A | 3/1976 | Yamaguchi et al. |
| 3,970,751 A | 7/1976 | Kano et al. |
| 3,974,171 A | 8/1976 | Hoffmann et al. |
| 4,001,404 A | 1/1977 | Hoffman et al. |
| 4,024,252 A | 5/1977 | Asada et al. |
| 4,056,610 A | 11/1977 | Barber, Jr. et al. |
| 4,067,970 A | 1/1978 | Cölln et al. |
| 4,076,806 A | 2/1978 | Lorenz et al. |
| 4,144,330 A | 3/1979 | Gsell et al. |
| 4,171,355 A | 10/1979 | Stubbs et al. |
| 4,622,315 A | 11/1986 | Dureja et al. |
| 4,634,690 A | 1/1987 | Dekeyser et al. |
| 4,668,511 A | 5/1987 | Aspirot et al. |
| 4,668,666 A | 5/1987 | Allan et al. |
| 4,902,510 A | 2/1990 | Garden |
| 5,064,639 A | 11/1991 | Dohara et al. |
| 5,130,135 A | 7/1992 | Van Tonder |
| 5,194,264 A | 3/1993 | Van Tonder |
| 5,229,122 A | 7/1993 | Chadwick et al. |
| 5,283,229 A | 2/1994 | Narayanan et al. |
| 5,296,227 A | 3/1994 | Norval et al. |
| 5,437,869 A | 8/1995 | Kelley |
| 5,576,308 A | 11/1996 | Henmi et al. |
| 5,591,727 A * | 1/1997 | Bencsits ..................... 514/68 |
| 5,632,999 A | 5/1997 | Miller |
| 5,641,499 A | 6/1997 | Bencsits |
| 5,645,845 A | 7/1997 | Neumann et al. |
| 5,707,638 A | 1/1998 | Lösel et al. |
| 5,711,956 A | 1/1998 | Wedlock et al. |
| 5,747,055 A | 5/1998 | Attali et al. |
| 5,912,003 A | 6/1999 | Chang |
| 5,925,367 A | 7/1999 | Angst et al. |
| 5,994,266 A | 11/1999 | Hobbs et al. |
| 6,045,816 A | 4/2000 | Narayanan et al. |
| 6,090,415 A | 7/2000 | Stadler et al. |
| 6,251,416 B1 | 6/2001 | Narayanan et al. |
| 6,270,784 B1 | 8/2001 | Mrusek et al. |
| 6,395,776 B1 | 5/2002 | Lösel et al. |
| 6,506,396 B1 | 1/2003 | Narayanan et al. |
| 6,514,510 B1 | 2/2003 | Fukuchi |
| 6,540,991 B2 | 4/2003 | Klassen et al. |
| 6,706,760 B2 | 3/2004 | Matsunaga |
| 6,719,959 B1 * | 4/2004 | Gonzalez et al. ............. 424/45 |
| 7,247,311 B2 | 7/2007 | Stein et al. |
| 2002/0098221 A1 | 7/2002 | Taranta et al. |
| 2002/0197295 A1 | 12/2002 | Stein et al. |
| 2004/0047889 A1 | 3/2004 | Greeson et al. |
| 2005/0042245 A1 | 2/2005 | Taranta et al. |
| 2005/0234119 A1 | 10/2005 | Soll et al. |
| 2005/0245582 A1 | 11/2005 | Cottrell et al. |
| 2006/0128796 A1 | 6/2006 | Fischer et al. |
| 2006/0147485 A1 | 7/2006 | Pedersen et al. |
| 2007/0072827 A1 | 3/2007 | Piccolo et al. |
| 2007/0196413 A1 | 8/2007 | Stern et al. |
| 2007/0276013 A1 | 11/2007 | Ebbinghaus et al. |
| 2007/0276014 A1 | 11/2007 | Cottrell et al. |
| 2008/0167374 A1 | 7/2008 | Stickler et al. |
| 2008/0199420 A1 | 8/2008 | Wendel et al. |

OTHER PUBLICATIONS

International Search Report issued on Nov. 16, 2009 for International Appln. No. PCT/US2009/058363.

* cited by examiner

*Primary Examiner* — Neil Levy
(74) *Attorney, Agent, or Firm* — Stroock & Stroock & Lavan LLP

(57) ABSTRACT

An insecticidal composition comprising stabilized pyrethrins or pyrethroids is provided. Such composition includes stabilizing effective amount of N,N-dialkyl fatty acid amide solvents and certain ultraviolet-light absorbers. In such composition, the pyrethrins or pyrethroid can retain their insecticidal activity for an acceptably long period of time. Therefore, an advantage of this invention is to provide a topical pyrethrins or pyrethroid based insecticide which can remain effective in light over a long time period. Another advantage of this invention is to provide a stabilized topical pyrethrins or pyrethroid insecticide insecticidal formulation containing a high concentration of the active pyrethrins or pyrethroid ingredient to minimize the volume of formulation required.

28 Claims, No Drawings

PHOTO-STABLE PEST CONTROL

CROSS-REFERENCE TO RELATED APPLICATIONS

This application is a national stage application under 35 U.S.C. 371 based on and claiming the benefit of International Application Ser. No. PCT/US2009/058363 filed on Sep. 25, 2009, which claims the benefit of and priority to U.S. Ser. No. 61/100,903, filed Sep. 29, 2008, the entire contents of which are incorporated herein by reference.

BACKGROUND OF INVENTION

This invention relates generally to insecticides and more particularly to a topical insecticide, such as one suitable to use on house pets such as cats and dogs.

The infestation of animals with fleas, ticks, flies and the like is highly undesirable. Accordingly, it has become common to administer both topical and internal insecticides to livestock and pets. Topical applications can be desirable, in that many insecticides are acceptably safe when used topically, but not when used internally.

Various topical insecticides have drawbacks. Some require a large volume to be applied to the animal. This can cause considerable mess and can lead to an unpleasant smell. Also, when the animal is a house pet, there is a further complication in that the insecticide should be safe for human contact. It should also not lead to staining of furniture, carpeting and the like. Finally, even if safe, topical insecticides for house pets should not be irritating or lead to rashes, hair loss or exhibit other unpleasant side effects.

Natural and synthetic pyrethrins (pyrethroids) are known to provide strong insecticidal activity. They provide quick knock down and kill a variety of arthropod pests while remaining safe to humans and animals. However, many pyrethrins and pyrethroids are photo labile and are not stable in the presence of air and light (sunlight more so than indoor light) due to degradation; hence they quickly lose their knockdown and kill efficacy when exposed to light.

Various stabilizers have been proposed for formulating pyrethrins containing insecticides. However, there remains a need for an improved pyrethrin formulation for the treatment of topical ectoparasites on animals capable of withstanding photo-degradation (specifically light in the ultra-violet wavelength) for a sustained period of time. For example, U.S. Pat. No. 3,943,239 discloses a insecticidal formulation containing pyrethrins and a stabilizer. Although it confers thermal stability, it fails to protect the pyrethrin formulation after 2 days in sunlight.

Accordingly, it is desirable to provide an improved pyrethrins formulation, which overcomes drawbacks of the prior art.

SUMMARY OF THE INVENTION

Generally speaking, in accordance with the invention, composition of stabilized pyrethrins or pyrethroids are provided. Such composition includes stabilizing effective amount of N,N-dialkyl fatty acid amide solvents and certain ultraviolet-light absorbers. In such composition, the pyrethrins or pyrethroid can retain their insecticidal activity for an acceptably long period of time.

Therefore, an advantage of this invention is to provide a topical pyrethrins or pyrethroid based insecticide which can remain effective in light over a long time period.

Another advantage of this invention is to provide a stabilized topical pyrethrins or pyrethroid insecticide insecticidal formulation containing a high concentration of the active pyrethrins or pyrethroid ingredient to minimize the volume of formulation required.

Other objects and features of the present invention will become apparent from the following detailed description.

DETAILED DESCRIPTION OF THE INVENTION

Compositions according to the invention provide an improved long-term efficacy against animal arthropod ectoparasites such as fleas and ticks by stabilizing the active insecticidal pyrethrins or pyrethroid compounds.

The present invention relates to a topical parasiticide comprising (a) an amount of a pyrethrins or pyrethroid effective as a parasiticide, (b) N,N-dialkyl fatty acid amide solvents, and (c) certain single or combination of ultraviolet-light absorbers in effective amounts and proportion to protect the insecticide from degradation by UV radiation.

The insecticidal active ingredient of the composition may be of any natural or synthetic pyrethrins (pyrethroids). Natural pyrethrins are natural extracts made from flowers of chrysanthemum plants. There are six types of pyrethrins: pyrethrin I and II, cinerin I and II, and jasmolin I and II. Generally all six types are referred to as pyrethrins. Synthetic pyrethrins, or pyrethroids, are synthetic analogs of natural pyrethrins. A non-exclusive list of pyrethroids may include allethrin, bifenthrin, cypermethrin, deltamethrin, resmethrin, phenothrin, tetramethrin, tralomethrin, and transfluthrin. Pyrethrins or pyrethroids are typically purchased in liquid form.

Pyrethrins are commercially available as a mixture containing contaminants and impurities such as waxes, esters, other extract ingredients and petroleum distillates. Typically a 60% pyrethrins concentrate is the highest pyrethrins concentration commercially available. Regardless of the starting concentration of the commercially available pyrethrins, the composition contains an effective amount of pyrethroid effective to control companion animal ectoparasites, preferably between 20% and 45%, and most preferably 25% of the total by weight of the composition.

Because composition in accordance with the invention can maintain their efficacy for relatively long periods of time compared to conventional compositions, less pesticide may be needed in a formulation embodying the present invention to achieve the same efficacy as compared to a formulation not stabilized in accordance of the invention.

UV-absorbers in accordance with preferred embodiments of the invention are selected from the group consisting Tinogard Q (tris (tetramethylhydroxypiperidinol) citrate), Tinogard TL (benzotriazolyl dodecyl p-creseol), Cibafast H (sodium benzotriazolyl butylphenol sulfonate (and) buteth-3 (and) tributyl citrate), Uvinul A (ethylhexyl methoxycinnamate) and Uvinul B (diethylamino hydroxybenzoyl hexyl benzoate), preferably a combination of Uvinul A and Uvinul B, more preferably a combination of Uvinul A and Uvinul B in a ratio of 30:70 and 40:60, and most preferably a combination of Uvinul A and Uvinul B in a ratio of 35:65.

The preferred ultraviolet absorbers are believed to provide a shielding effect on the pyrethrins to prevent breakdown in light, thereby extending the effective life of the pyrethroid composition in sunlight after it has been applied to the skin or fur of the animal. The UV-absorber should be present in an amount effective to prevent significant reduction of the insecticidal activity, and preferably makes up 5% of the total by weight of the composition.

The solvent in the composition may be a N,N-dialkyl fatty acid amide, preferably Hallcomid M8 (N,N dimethyl octanamide), Hallcomid M10 (N,N dimethyl decanamide), or a combination of Hallcomid M8 and Hallcomid M10. The presence of N,N-dialkyl fatty acid amides appear to contribute to the stability of the composition of the invention. The solvent to active ratio can be up to 10:1, preferably 1:4 to 1:5. In terms of total volume, the solvent is present in at least an amount sufficient to completely solubilize the ingredients, preferably between 0.10% to 50% of total composition by weight, and most preferably 14% of the total composition.

In the preparation of a formulation for use on animals, there are several parameters that should be considered. These are:
(a) Concentration high enough to minimize the volume of the topical applied to the animal (one would not want to put 20 ml, e.g., onto a small dog).
(b) Concentration low enough to achieve effective translocation of the topical insecticide over the animal's skin.
(c) The formulation should be stable for six months at 40° F. and 75% relative humidity, room temperature and –10 F. This helps ensure that the formulation remains stable under the conditions that it could meet in commerce.
(d) Safe to use on the intended animal—particularly non-irritating to at least the intended animal, since the product is applied to the skin. Also safe if ingested by the animal; ingestion can occur when pets groom themselves.
(e) Safe to use by the consumer.
(f) Efficacious in use—should kill greater than 90% of the fleas and ticks up to 28 days and kill or eliminate the ectoparasites.
(g) Efficacy would be reduced if crystallization occurred in the package.
(h) Needs to be aesthetically pleasing—"no oily drop" on the animal when applied.
(i) Fast drying to reduce the chance of the animal shaking off the liquid thereby reducing efficacy.
(j) Microbiologically stable.

It can be advantageous for the insecticidal formulations of the invention to contain an enzyme inhibitor or a synergist such as piperonyl butoxide, which can increase the efficacy of the formulation. The topical formulations also contain one or more compounds to increase the efficacy and to reduce the irritation of pyrethroid insecticides to the skin of animals. The formulation can advantageously contain spreading agents such as organic esters, fragrances, and/or antioxidants.

Polymers such as agar, gelatin, alginate, and cationic polymers such as cationic guar, cationic cellulose, cationic acrylates, and polyoxymethylene urea may also be added to provide enrobing of the insecticide to improve safety and adhesion to skin and hair. In practice, an effective amount of the insecticidal compositions as described herein may be applied to a companion animal, preferably a dog or a cat, as a foaming shampoo, dip, aerosol spray, pump spray, powder, lotion, emulsifiable concentrate, aqueous or liquid flowable, suspension concentrate and by any other methods suitable for administering topical compositions to animals.

The following examples are given for purposes of illustration only and are not intended to be construed in a limiting manner.

EXAMPLE 1

Formulation I Preparation and Stability Measurements

Formulation I was prepared by mixing 10% pyrethrins, 30% Hallcomid M10, 45% organic ester solvent, and 5% Uvinul A and Uvinul B mixture (whereby the ratio of Uvinul A and Uvinul B is 35:65).

(Note: all references to pyrethrins are with the understanding that the concentration of the raw material added to a formula contains 50% pyrethrins. Thus total formulas will not add up to 100%.)

To test the effectiveness of the UV-protection formulation, one batch of Formulation I was stored in darkness while another batch of Formulation I was exposure to 290-400 nm wavelength UV light for five weeks. The amount of pyrethrins remaining was measured weekly through high performance liquid chromatography. For the sample of pyrethrins stored in darkness, 98.69% of the initial pyrethrins remained after three weeks, and 91.19% of the initial pyrethrins remained after five weeks.

For the sample of pyrethrins exposed to UV light, 91.85% of the initial pyrethrins remained available after three weeks and 83.14% of the initial pyrethrins remained available after five weeks. The amount of pyrethrins remaining was considered comparable to the batch stored in darkness.

The same testing was applied to a control formulation (Control I) containing 10% pyrethrins, 30% Hallcomid M10, 50% organic ester, and no UV-absorbing component. After three weeks of exposure to the UV light, only 58.34% of the initial pyrethrins remained available. After five weeks of exposure to the same UV light, only 46.36% of the initial pyrethrins remained available. When the control formulation was stored in darkness, 97.65% of the initial pyrethrins remained available after three weeks and 94.76% of the initial pyrethrins remained available after five weeks.

EXAMPLE 2

Formulation II Preparation and Stability Measurements

Formulation II was prepared by mixing 40% pyrethrins, 7.5% Hallcomid M10, 7.5% organic ester, and 5% Uvinul A and Uvinul B mixture (whereby the ratio of Uvinul A and Uvinul B is 35:65) and tested by the method discussed in Example 1. After three weeks of exposure to the UV light, 92.22% of the initial pyrethrins remained available. After five weeks of exposure to the same UV light, 87.22% of the initial pyrethrins remained available.

The same testing is applied to a control formulation (Control II) containing 40% pyrethrins, 10% Hallcomid M10, 10% organic ester, and no UV-absorbing component. After three weeks of exposure to UV light, only 73.90% of the initial pyrethrins remained available. After five weeks of exposure to UV light, only 64.94% of the initial pyrethrins remained available.

EXAMPLE 3

Formulation III Preparation and Stability Measurements

Formulation III consistent was prepared by mixing 30% pyrethrins, 17.5% Hallcomid M10, 17.5% organic ester, and 5% Uvinul A and Uvinul B mixture (whereby the ratio of Uvinul A and Uvinul B is 35:65). After three weeks of exposure to the UV light, 92.13% of the initial pyrethrins remained available. After five weeks of exposure to the same UV light, 86.76% of the initial pyrethrins remained available.

As a further point of comparison, a photo-stabilized formulation disclosed in U.S. Pat. No. 5,591,727 is prepared: 0.03% ethyl hexyl p-dimenthylamino benzoate (ESCALOL 507), 0.03% tirbutyl citrate, 2% lecithin, 0.06% pyrethrins, and 97.88% water is combined.

After one week of exposure to the UV light, 86.21% of the initial pyrethrins remained available. After two weeks of exposure to the same UV light, only 18.97% of the initial pyrethrins remained available. After three weeks of exposure, only 15.50% of the initial pyrethrins remained available. Moreover, this formulation was not stable even when stored in darkness. 84.48%, 29.30% and 29.30% of the pyrethrins remained after one, two, and three weeks of store in darkness, respectively.

Table 1 is a comparison of active pyrethrins remaining over a five week period, between Formulation I, Formulation II, Formulation III, Control I, and Control II.

TABLE 1

| Formulation Pyrethrins/M-10/Organic Ester/Uvinul A + B | Storage Condition | Two Weeks | Three Weeks | Four Weeks | Five Weeks |
|---|---|---|---|---|---|
| Control I 10/30/50/0 | Dark UV | 97.11 82.00 | 97.65 58.34 | 92.96 59.66 | 94.76 46.36 |
| Control II 40/10/10/0 | Dark UV | 98.65 82.00 | 94.82 58.34 | 91.40 59.66 | 99.34 46.36 |
| Formulation I 10/30/45/5 | Dark UV | 90.69 95.11 | 98.69 91.85 | 94.82 87.94 | 91.19 83.14 |
| Formulation II 40/7.5/7.5/5 | Dark UV | 92.24 98.22 | 95.48 92.22 | 92.42 83.75 | 93.55 87.22 |
| Formulation III 30/17.5/17.5/5 | Dark UV | 97.15 97.43 | 96.31 92.13 | 96.26 89.69 | 96.89 86.76 |
| U.S. Pat. No. 5,591,727 | Dark UV | 29.30 18.97 | 29.30 15.50 | | |

As can be seen in Table 1, pyrethrins remained effective when stored in darkness. However, in the presence of UV radiation, only those with Uvinul A and Uvinul B retained above 90% availability at the three weeks mark and above 80% availability at the five weeks mark.

EXAMPLE 4

Formulation IV Preparation and Stability Measurements

Formulation IV was prepared by mixing 20% pyrethrins, 27.5% Hallcomid M10, 27.5% organic ester, and 5% Uvinul A and Uvinul B mixture (whereby the ratio of Uvinul A and Uvinul B is 35:65) and tested by the method discussed in Example 1.

A control formulation (Control III) is prepared by mixing 20% pyrethrins, 27.5% seed oil, 27.5% organic ester, 5% Uvinul A and Uvinul B mixture (whereby the ratio of Uvinul A and Uvinul B is 35:65) and no Hallcomid M10.

The efficacy of Formulation II, Formulation IV, and Control III were subjected to a flea and tick mortality test. Each formulation was diluted down to ⅕ of the original concentration and 0.1 ml of the diluted formulation was applied to two disks and allowed to dry overnight. For each formulation, one disk was stored in darkness and one disk was stored under exposure to the UV light between tests.

To perform the actual test, each disk was treated and allowed to dry overnight. Testing began 18 hours later and each disc was deposited in a vial, which was then inoculated with 100 ticks and 100 fleas. To perform the actual test, each disk was deposited in an enclosed vial containing 100 ticks and 100 fleas. Between Test Days, treated disks were returned to storage. The number of dead and moribund ticks and fleas were counted and recorded. The test was performed at day 0, 7, 14, 21, 28, and 35.

Table 2 is a comparison of flea and tick dead and moribund rate of Formulation II, Formulation IV, and Control III. For each formulation, the count of dead or moribund ticks and fleas are separately listed. The count of dead tick and flea are listed in parenthesis.

TABLE 2

| Pyrethrins/M-10/ Organic Ester/ Uvinul A + B | Dead + Moribund Sample | | | | | | | | | | | |
|---|---|---|---|---|---|---|---|---|---|---|---|---|
| | Initial | | Day 7 | | Day 14 | | Day 21 | | Day 28 | | Day 35 | |
| | T | F | T | F | T | F | T | F | T | F | T | F |
| Formulation II (UV) 40/7.5/7.5/5 | 100 (100) | 98 (18) | 100 (100) | 100 (20) | 100 (100) | 92 (36) | 100 (17) | 62 (16) | 100 (0) | 28 (10) | 90 (0) | 10 (0) |
| Formulation II (Dark) 40/7.5/7.5/5 | 100 (100) | 98 (24) | 100 (100) | 100 (32) | 100 (100) | 100 (32) | 100 (0) | 90 (40) | 100 (0) | 96 (18) | 100 (0) | 100 (22) |
| Formulation IV (UV) 20/27.5/27.5/5 | 100 (100) | 100 (32) | 100 (100) | 98 (24) | 100 (94) | 100 (40) | 100 (10) | 80 (24) | 100 (10) | 18 (2) | 91 (7) | 22 (0) |
| Formulation IV (Dark) 20/27.5/27.5/5 | 100 (100) | 100 (40) | 100 (93) | 100 (32) | 100 (97) | 100 (40) | 100 (0) | 96 (34) | 100 (0) | 96 (24) | 100 (0) | 94 (20) |
| Control III (UV) 20/0/27.5/5 | 100 (100) | 72 (26) | 100 (100) | 30 (2) | 100 (100) | 74 (16) | 100 (47) | 0 (0) | 77 (7) | 10 (2) | 27 (0) | 4 (0) |
| Control III (Dark) 20/0/27.5/5 | 100 (100) | 72 (26) | 100 (96) | 70 (0) | 100 (100) | 90 (26) | 100 (0) | 44 (16) | 100 (0) | 38 (10) | 100 (20) | 86 (34) |

T = Tick
F = Flea
( ) = % Dead

As can be seen from Table 2, by day 28 and day 35, the number of dead or moribund tick dropped to 77 and 27 for Control III (without Hallcomid M10) exposed to UV, respectively. In contrast, the disks treated with Formulation II and Formulation IV maintained 90-plus flea kill by day 35 notwithstanding UV exposure. Similarly, in the instance of residual activity against fleas, Control III disk consistently showed less dead and moribund fleas than Formulation II and Formulation IV. The comparison between Formulation IV and Control III demonstrates that Hallcomid M10 contributes to some UV stabilization in addition to the presence of Uvinul A and Uvinul B.

Furthermore, a comparison of Formulation II and Formulation IV shows that, although Formulation IV contains 50% of the pyrethrins active ingredient found in Formulation II (20% versus 40%), the efficacy measured by dead and moribund tick and flea is comparable throughout the 35 days test period. This comparison shows that the UV stabilizer permits the use of less active pyrethrins ingredients to achieve the same insecticidal activity.

EXAMPLE 5

Formulation V Preparation

Formulation V was prepared by mixing 10% pyrethrins, 30% Hallcomid M10, 45% organic ester, and 5% UV-protection agent, where the UV-protection agent may be Uvinul A and Uvinul B, Cibafast H, Tinogard Q, or Tinogard TL.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description shall be interpreted as illustrative and not in a limiting sense.

It is also to be understood that the following embodiments are intended to cover all of the generic and specific features of the invention herein described and all statements of the scope of the invention which, as a matter of language, might be said to fall there between.

Particularly it is to be understood that in said embodiments, ingredients or compounds recited in the singular are intended to include compatible mixtures of such ingredients wherever the sense permits.

We claim:

1. A topical formulation comprising a first active ingredient comprising at least one insecticidal pyrethrin or pyrethroid, a solvent comprising N,N dimethyl octanamide or N,N dimethyl decanamide, and at least one UV-absorbing component selected from the group consisting of tris (tetramethylhydroxypiperidinol) citrate, benzotriazolyl dodecyl p-cresol, sodium benzotriazolyl butylphenol sulfonate (and) buteth-3 (and) tributyl citrate, and a combination of ethylhexyl methoxycinnamate and diethylamino hydroxybenzoyl hexyl benzoate.

2. The topical formulation of claim 1, wherein the solvent comprises a combination of N,N dimethyl octanamide and N,N dimethyl decanamide.

3. The topical formulation of claim 1, wherein the solvent comprises N,N dimethyl decanamide.

4. The topical formulation of claim 1, wherein the solvent comprises N,N dimethyl octanamide.

5. The topical formulation of claim 1, wherein the first active ingredient comprises a natural pyrethrin.

6. The topical formulation of claim 1, wherein the first active ingredient comprises a synthetic pyrethroid.

7. The topical formulation of claim 1, wherein the first active ingredient is between about 1% and about 50% by weight of the total formulation.

8. The topical formulation of claim 1, wherein the N,N dialkyl fatty acid amide solvent is between about 1% and about 40% by weight of the total formulation.

9. The topical formulation of claim 1, wherein the UV-absorbing component is between about 1% and about 10% by weight of the total formulation.

10. The topical formulation of claim 1, wherein the solvent and the first active ingredient are in a ratio between about 1:4 and about 1:5.

11. The topical formulation of claim 6, wherein the synthetic pyrethroid is phenothrin.

12. The topical formulation of claim 1, wherein the UV-absorbing component comprises a combination of ethylhexyl methoxycinnamate and diethylamino hydroxybenzoyl hexyl benzoate in a ratio between about 30:70 and about 40:60.

13. The topical formulation of claim 12, wherein the UV-absorbing component comprises a combination of ethylhexyl methoxycinnamate and diethylamino hydroxybenzoyl hexyl benzoate in a ratio of about 35:65.

14. The topical formulation of claim 9, wherein the UV-absorbing component is about 5% by weight of the total formulation.

15. The topical formulation of claim 1, wherein the UV-absorbing component is tris (tetramethylhydroxypiperidinol) citrate.

16. The topical formulation of claim 1, wherein the UV-absorbing component is benzotriazolyl dodecyl p-cresol.

17. The topical formulation of claim 1, wherein the UV-absorbing component is sodium benzotriazolyl butylphenol sulfonate (and) buteth-3 (and) tributyl citrate.

18. The topical formulation of claim 1, wherein the UV-absorbing component is a combination of ethylhexyl methoxycinnamate and diethylamino hydroxybenzoyl hexyl benzoate.

19. The topical formulation of claim 1, wherein the formulation consists essentially of a first active ingredient comprising at least one insecticidal pyrethrin or pyrethroid, a solvent comprising N,N dimethyl octanamide or N,N dimethyl decanamide, and at least one UV-absorbing component selected from the group consisting of tris (tetramethylhydroxypiperidinol) citrate, benzotriazolyl dodecyl p-cresol, sodium benzotriazolyl butylphenol sulfonate (and) buteth-3 (and) tributyl citrate, and a combination of ethylhexyl methoxycinnamate and diethylamino hydroxybenzoyl hexyl benzoate.

20. The topical formulation of claim 19, wherein the solvent comprises a combination of N,N dimethyl octanamide and N,N dimethyl decanamide.

21. The topical formulation of claim 19, wherein the first active ingredient comprises a synthetic pyrethroid or a natural pyrethrin.

22. The topical formulation of claim 19, wherein the UV-absorbing component is between about 1% and about 10% by weight of the total formulation.

23. The topical formulation of claim 19, wherein the first active ingredient is phenothrin.

24. The topical formulation of claim 19, wherein the UV-absorbing component comprises a combination of ethylhexyl methoxycinnamate and diethylamino hydroxybenzoyl hexyl benzoate in a ratio between about 30:70 and about 40:60.

25. The topical formulation of claim 24, wherein the UV-absorbing component is a combination of ethylhexyl methoxycinnamate and diethylamino hydroxybenzoyl hexyl benzoate in a ratio of about 35:65.

26. The topical formulation of claim 19, wherein the UV-absorbing component is about 5% by weight of the total formulation.

27. The topical formulation of claim 19, wherein the solvent comprises N,N dimethyl decanamide.

28. The topical formulation of claim 19, wherein the solvent comprises N,N dimethyl octanamide.

* * * * *